United States Patent
Tsubouchi

(10) Patent No.: US 10,531,947 B2
(45) Date of Patent: Jan. 14, 2020

(54) GREAT VESSEL GRAFT SUTURING AID

(71) Applicant: TERUMO CARDIOVASCULAR SYSTEMS CORPORATION, Ann Arbor, MI (US)

(72) Inventor: Takeshi Tsubouchi, Dexter, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 224 days.

(21) Appl. No.: 15/679,502

(22) Filed: Aug. 17, 2017

(65) Prior Publication Data
US 2018/0055621 A1 Mar. 1, 2018

Related U.S. Application Data

(60) Provisional application No. 62/378,981, filed on Aug. 24, 2016.

(51) Int. Cl.
| A61F 2/07 | (2013.01) |
| A61F 2/95 | (2013.01) |
| A61F 2/06 | (2013.01) |
| A61F 2/90 | (2013.01) |
| A61B 17/11 | (2006.01) |

(52) U.S. Cl.
CPC ............... *A61F 2/07* (2013.01); *A61B 17/11* (2013.01); *A61F 2/95* (2013.01); *A61F 2/064* (2013.01); *A61F 2/90* (2013.01)

(58) Field of Classification Search
CPC ...... A61F 2/07; A61F 2/95; A61F 2/90; A61F 2/064; A61B 17/11; A61B 2017/1107; A61B 2017/1103; A61B 17/1114; A61B 17/32; A61B 17/34; A61B 2017/00243; A61B 17/115; A61B 2017/111; A61B 2017/1121; A61B 2017/00278; A61B 17/32053
See application file for complete search history.

(56) References Cited

U.S. PATENT DOCUMENTS

| 5,503,617 A | 4/1996 | Jako |
| 5,885,238 A | 3/1999 | Stevens et al. |
| 7,717,844 B2 | 5/2010 | Cohn |
| 2004/0030348 A1 | 2/2004 | Peterson et al. |
| 2004/0050393 A1 | 3/2004 | Golden et al. |
| 2005/0251175 A1* | 11/2005 | Weisenburgh, II ........................ A61B 17/0401 606/153 |

(Continued)

*Primary Examiner* — Katrina M Stransky
(74) *Attorney, Agent, or Firm* — Darryl Newell; MacMillan, Sobanski & Todd, LLC

(57) ABSTRACT

A stabilization tool supports a blood vessel for suturing during cardiovascular surgery. The support vessel may typically be part of an artificial graft used in replacing an aortic arch. The stabilization tool has a central shaft with a mounting element at a first end. A plurality of retractable arms have their distal ends affixed to a second end of the central shaft. The retractable arms are movable between a nested position flanking the central shaft and a range of extended positions wherein proximal ends of the retractable arms are spaced away from the central shaft. A closing ring is slidable over the retractable arms from a deployed position adjacent the second end of the central shaft to a retracted position spaced away from the second end to move the retractable arms.

12 Claims, 6 Drawing Sheets

(56) References Cited

U.S. PATENT DOCUMENTS

| | | |
|---|---|---|
| 2006/0241748 A1 | 10/2006 | Lee et al. |
| 2006/0253137 A1* | 11/2006 | Ortiz ............... A61B 17/11 606/153 |
| 2007/0021759 A1* | 1/2007 | Griffith ............ A61B 17/11 606/153 |
| 2007/0282355 A1 | 12/2007 | Brown et al. |
| 2014/0276975 A1 | 9/2014 | Argentine |

* cited by examiner

US 10,531,947 B2

GREAT VESSEL GRAFT SUTURING AID

CROSS REFERENCE TO RELATED APPLICATIONS

This application claims priority to provisional application Ser. No. 62/378,981, filed on Aug. 24, 2016, which is incorporated herein by reference in its entirety.

BACKGROUND OF THE INVENTION

In great vascular surgery, a patient's vessel (e.g., aortic arch) may be replaced with a vascular graft made with fabric. Due to size variations or differences in vessel diameters (e.g., between the distal end and the proximal end of the graft), suturing at a large diameter of the graft can be challenging. Since the graft is unpressurised and unsupported while suturing, it has been very difficult to achieve a desired shape after suturing. Sometimes the sutured end is either too short (thereby introducing stretch damage on the vessel) or too loose (thereby causing wrinkles which may increase blood clotting). It is very important to be able to see the full circular perimeter of the vascular graft in order to identify the best suture points and to evenly distribute tension.

SUMMARY OF THE INVENTION

This invention provides a suitable circular-shaped support during suturing while providing excellent position adjustability without impairing side access or blocking the working space. Additionally, the holding mechanism has a closeable (i.e., foldable) frame to make the holder very thin for removal after sewing. The surgeon can leave a few stitches loose and then fold (i.e., collapse) the fixture in order to remove the tool from the vascular graft.

The invention comprises a tool for a major vascular operation. The tool has at least 3 foldable (i.e., retractable) supports attached to a main shaft which will expand for a custom fit to the inside diameter of the vessel or vascular graft, creating a stationary hold. A ring-shaped cover slides over and closes the foldable support in the closed configuration. The ring may be pulled by a wire, string, or other linkages.

In one particular aspect of the invention, a stabilization tool comprises a central shaft with a mounting element at a first end. A plurality of retractable arms have their distal ends affixed to a second end of the central shaft. The retractable arms are movable between a nested position flanking the central shaft and a range of extended positions wherein proximal ends of the retractable arms are spaced away from the central shaft. A closing ring is slidable over the retractable arms from a deployed position adjacent the second end of the central shaft to a retracted position spaced away from the second end to move the retractable arms.

DETAILED DESCRIPTION OF PREFERRED EMBODIMENTS

The invention provides an assistant tool particularly adapted to be used in vascular graft operation in order to secure visibility and working space for anastomosis. By using this tool with a stabilizer support arm (e.g., the Hercules™ Stabilizer Arm available from Terumo Cardiovascular Systems of Ann Arbor, Mich.), a surgeon can manipulate and secure an arch graft to a specific position for good visibility and suture without additional human assistance.

Figure 1:
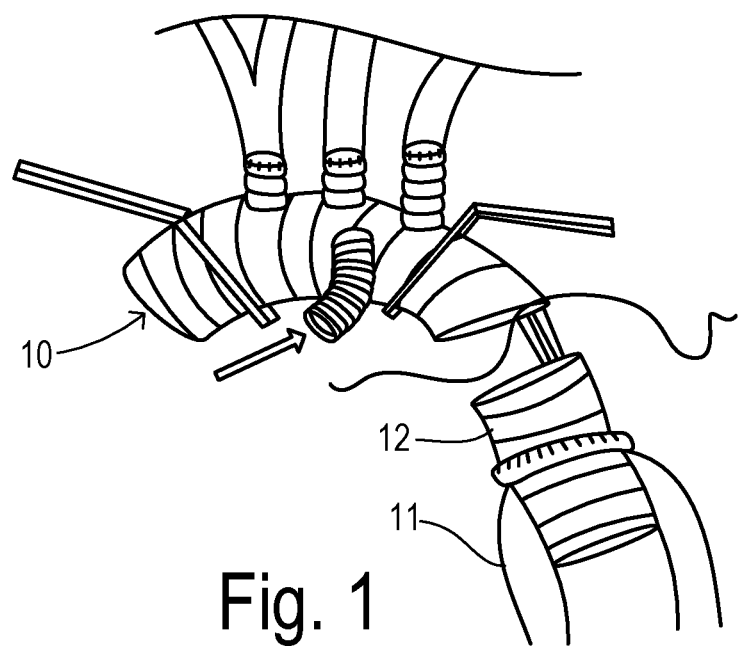
FIG. 1 illustrates one type of procedure for anastomosing an aortic arch graft.
Figure 2:
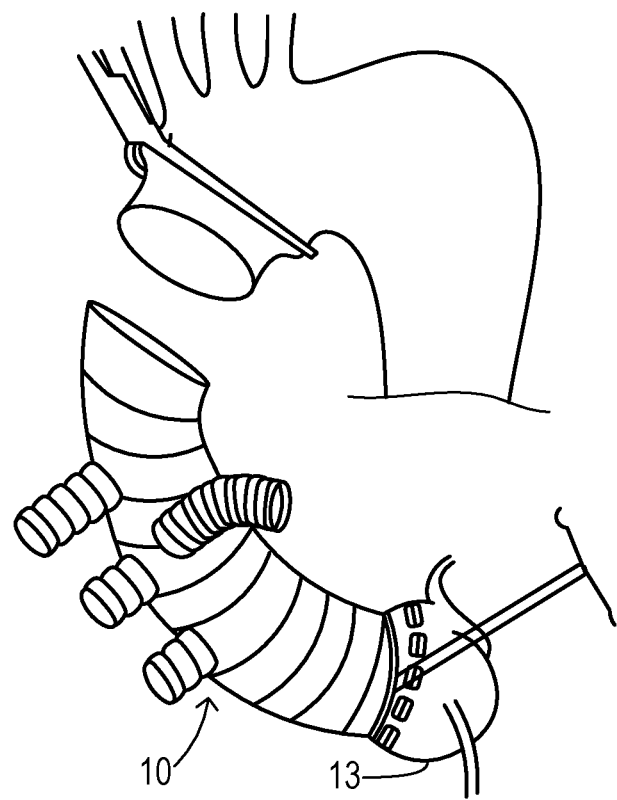
FIG. 2 illustrates another type of procedure for anastomosing an aortic arch graft.

FIGS. 1 and 2 illustrate suturing of a branched graft 10 to replace an aortic arch. In FIG. 1, graft 10 is being sutured to a descending aorta 11 via an extension graft 12. In FIG. 2, graft 10 is being sutured to an ascending aorta 13. These stages of an aortic arch replacement and other types of vascular surgery can be performed more effectively when a vessel to be sutured (either an artificial graft or a living vessel) can be held open near to its natural condition during anastomosis.

Figure 3:
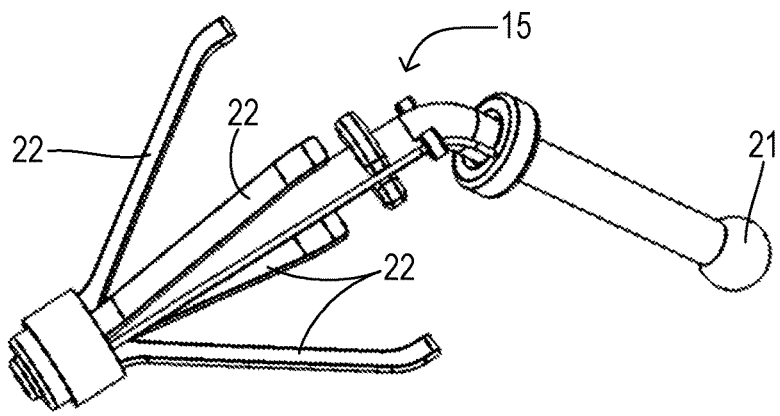
FIG. 3 is a perspective view of a stabilization tool according to one embodiment of the invention with retractable arms deployed to extended positions.
Figure 4:
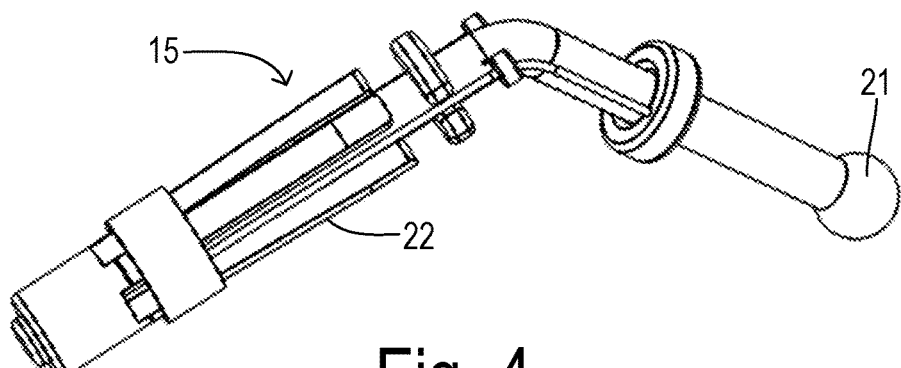
FIG. 4 is a perspective view of the stabilization tool of FIG. 3 with the retractable arms retracted to nested positions.
Figure 5:
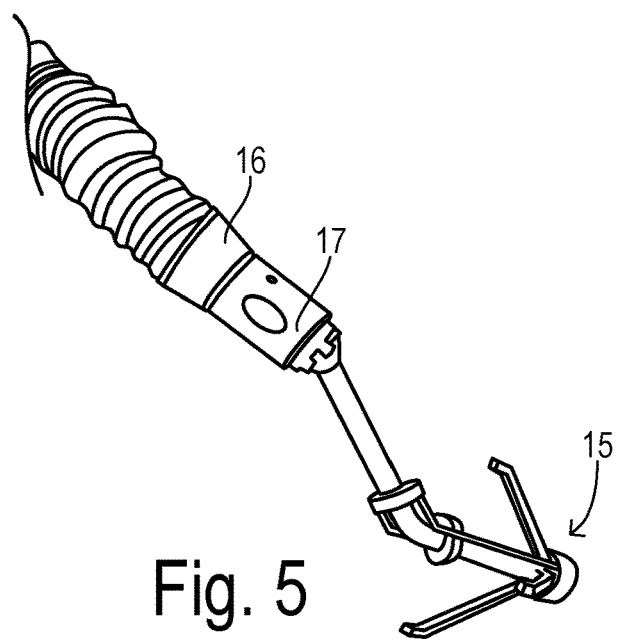
FIG. 5 is a perspective view of the stabilization tool of FIG. 3 mounted on a support arm.
Figure 6:
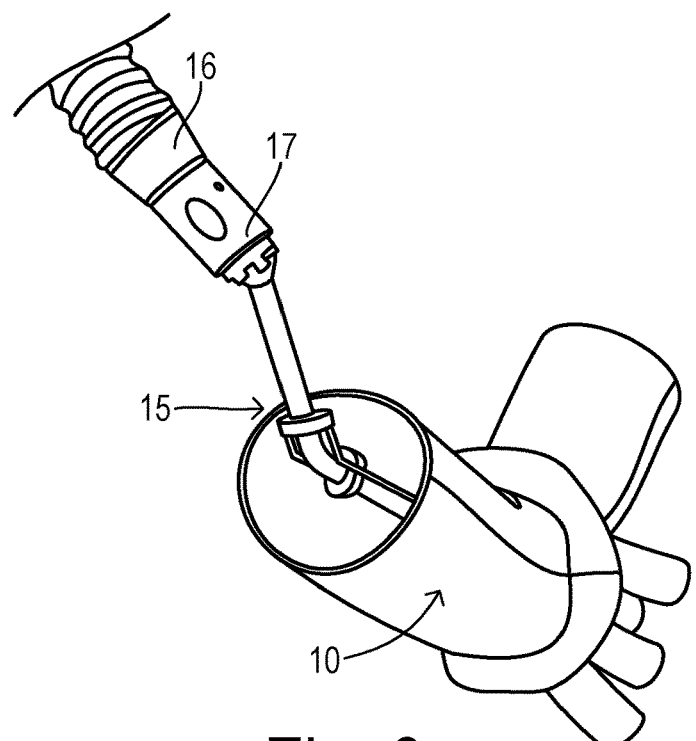
FIG. 6 is a perspective view of the stabilization tool mounted on a support arm and disposed within a graft for holding the graft open during suturing.

FIGS. 3 and 4 are open and closed configurations of an "inside support umbrella-frame" stabilization tool 15. At a distal end of tool 15, a plurality of retractable arms 22 are movable to a nested position (FIG. 4), a maximum extended position (FIG. 3), and a range of extended positions between them. At a proximal end of tool 15, a central shaft ends with a ball 21 as a mounting element that is adapted to be captured on a support arm using a conventional "quick connect" mechanism. FIG. 5 shows tool 15 mounted at the end of a support arm. For illustration, tool 15 is shown with the arm is an extended position although they would typically be retracted to the nested position prior to placement inside the vessel being sutured. FIG. 6 shows the supported tool 15 holding open graft 10.

Figure 8:
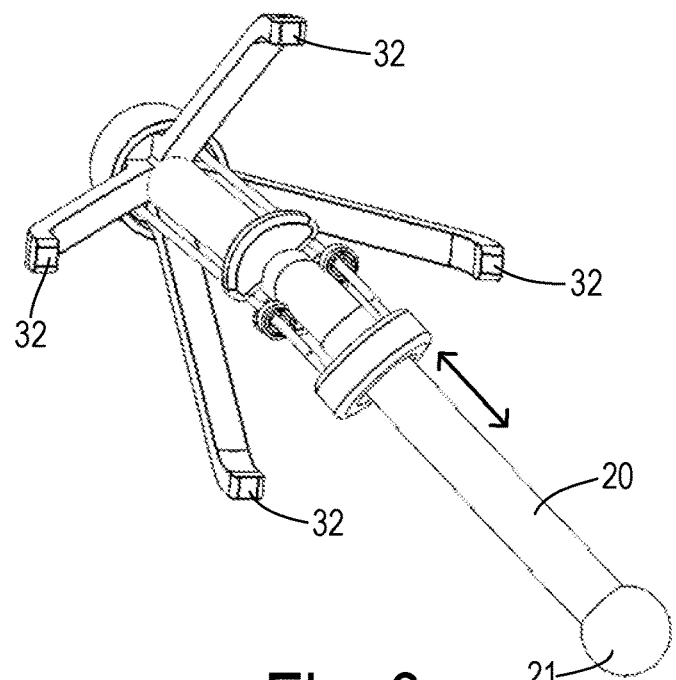
FIG. 8 is another perspective view of the stabilization tool.
Figure 7:
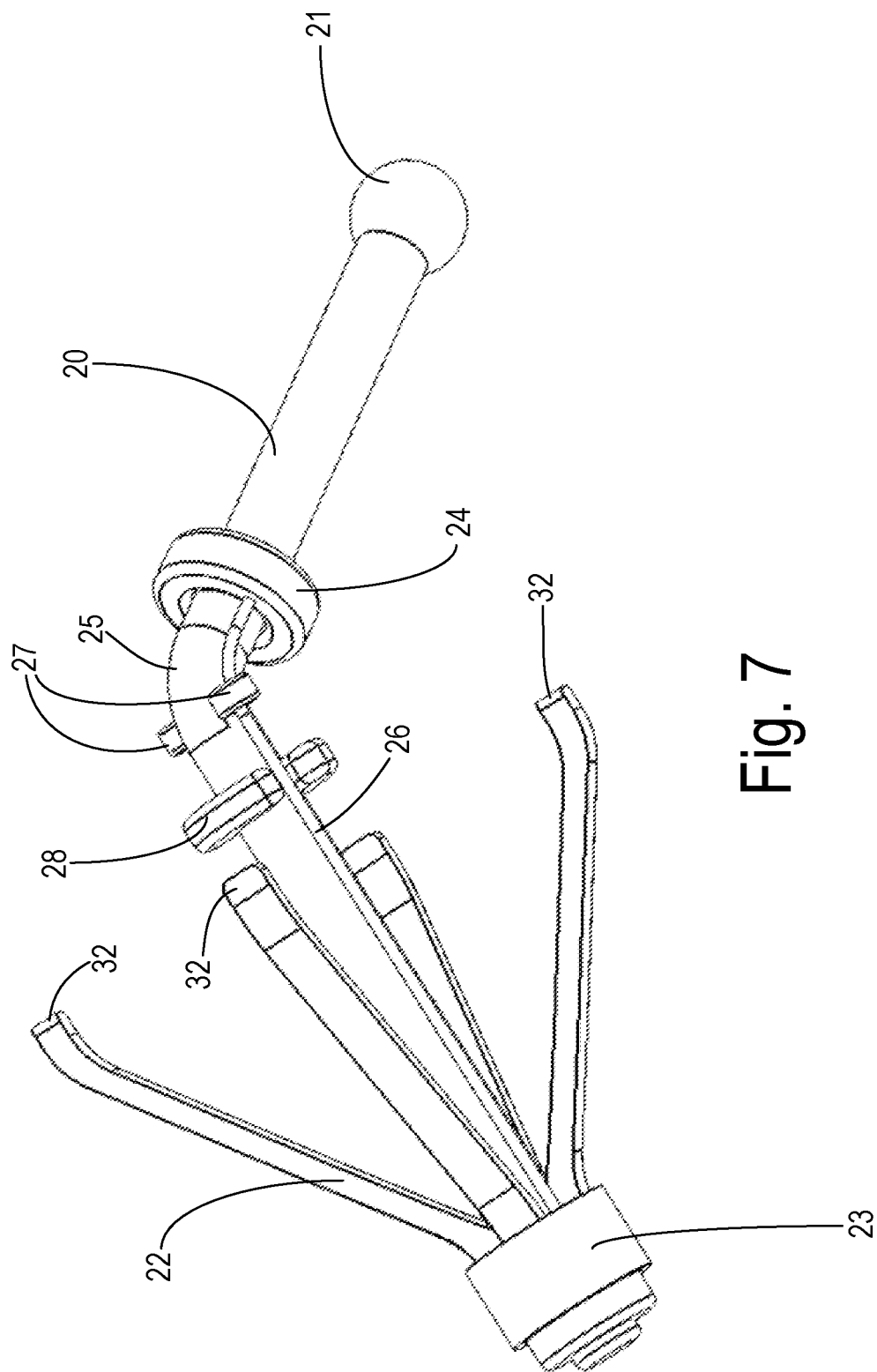
FIG. 7 is a perspective view showing the stabilization tool in greater detail.
Figure 9:
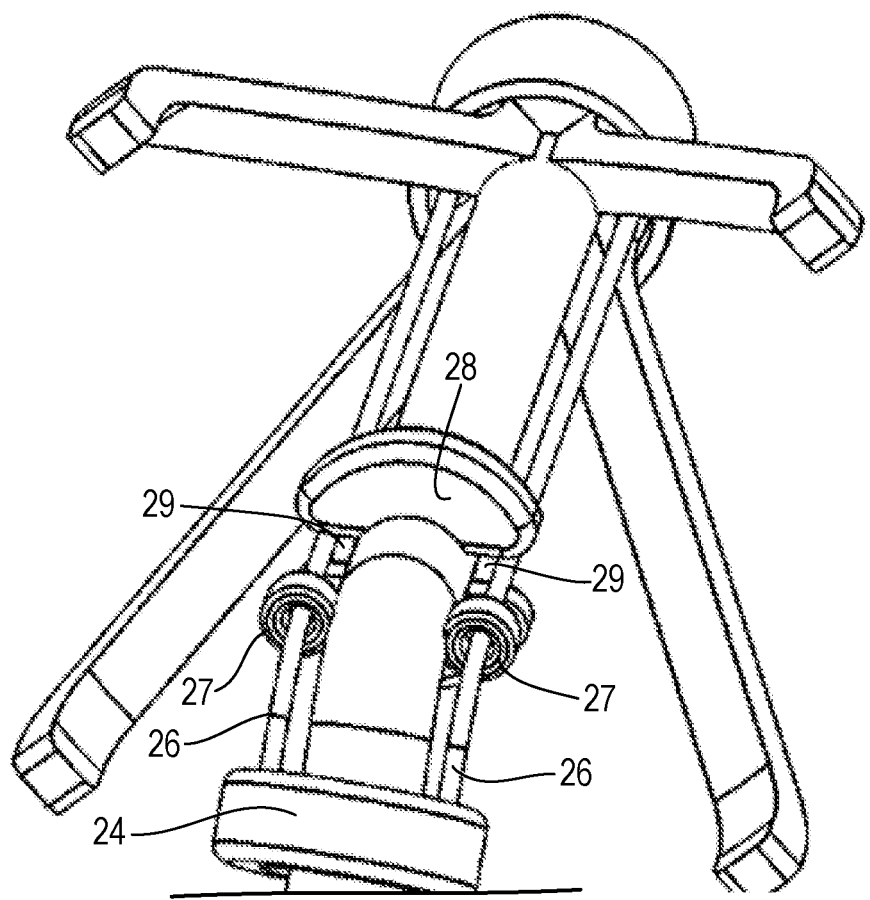
FIG. 9 is a close-up view of one embodiment of the opening/closing mechanism with the arms in an extended position.

FIGS. 7-9 show the open configuration of tool 15 in greater detail. A main, central shaft 20 is bent or angled at an intermediate bend 25. Shaft 20 has mounting ball 21 at the proximal end and a set of retractable spring arms 22 at the distal end. There may be three or more arms 22, preferably there are four. Arms 22 are arranged to naturally spring outward in a maximum extended position as shown.

Figure 11:
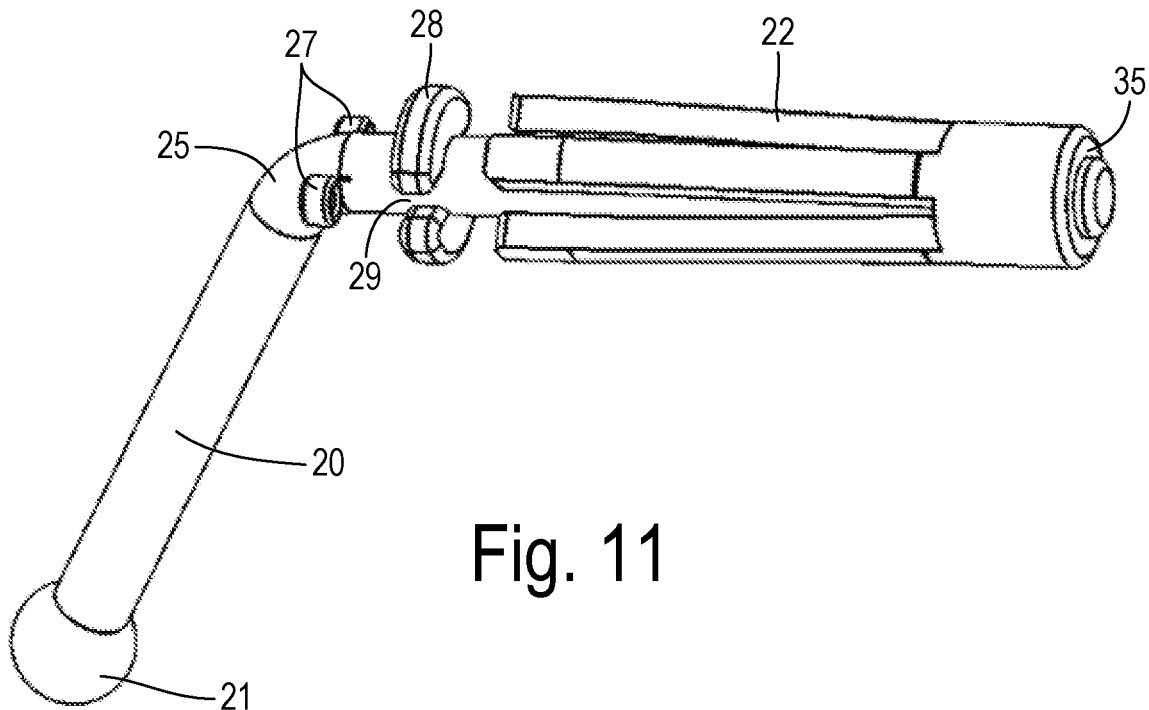
FIG. 11 is a side view of a portion of the tool showing the arms in a nested position even though the closing ring is not shown.

Proximal ends 32 of retractable arms 22 are spaced away from central shaft 20 when in the extended positions. A closing ring 23 has an inside diameter configured to slide over arms 22 in order to retract arms 22 into a closed configuration with each arm 22 at a nested position flanking shaft 20 (FIGS. 4 and 11). Closing ring 23 is connected to a manual control ring 24 by push-pull cables or wires 26 that extend through fixed eyelets 27 and a pair of aligned slots 29 in a hub 28.

Closing ring 23 is slidable over retractable arms 22 from a deployed position adjacent the distal end of central shaft 20 to a retracted position spaced away from the distal end. Control ring 24 slides along central shaft 20 under manual control of a surgeon. Push-pull cables 26 connect control ring 24 and closing ring 23 so that motion of control ring 24 is replicated by closing ring 23 to reconfigure retractable arms 22 between the nested position and an extended position within the range of extended positions. In order to provide bidirectional movement using control ring 24, cables 26 should be sufficiently stiff to be able to push closing ring 23 from the retracted position to the deployed position. Thus, cables 26 may preferably be comprised of metallic wire (such as stainless steel) or a molded thermoplastic (such as TPE or TPO). Alternatively, tool 15 could be reconfigured from the closed to open position without relying on cables 26 by pulling directly on closing ring 23 since it may be acceptable to deploy arms 22 prior to placement within the vessel.

Figure 10:
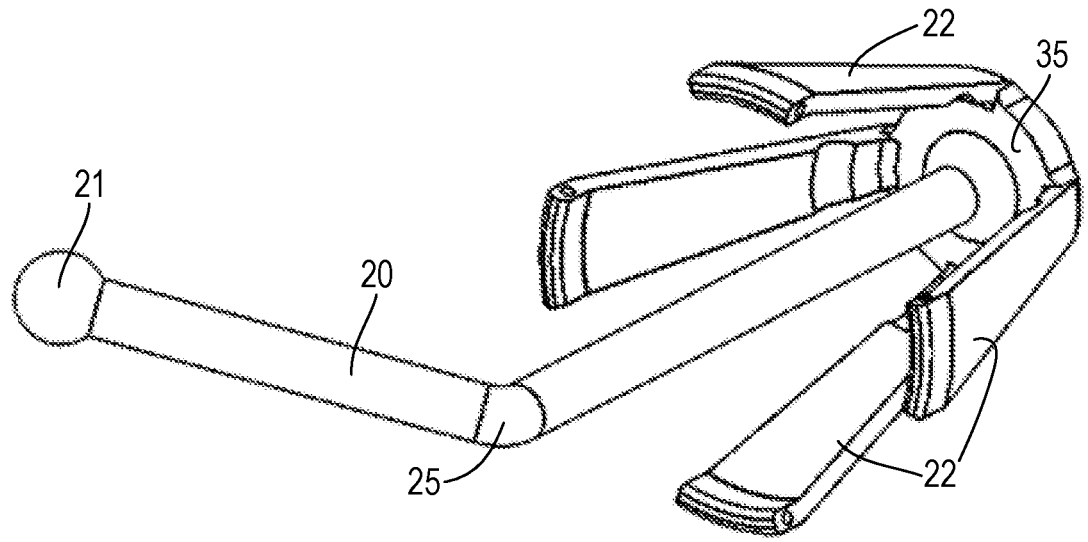
FIG. 10 is a perspective view of a central shaft with integral retractable arms according to one preferred embodiment.

FIG. 10 shows the natural, undeflected position of retractable spring arms 22 in relation to central shaft 20. An end plate 35 joins shaft 20 to arms 22. Plate 35, shaft 20, and arms 22 can all be part of an integrally molded unit (i.e., all formed of the same plastic). Arms 22 can alternatively be made of metal (such as a spring grade stainless steel), with arms 22 being insert molded into plate 35.

Figure 12:
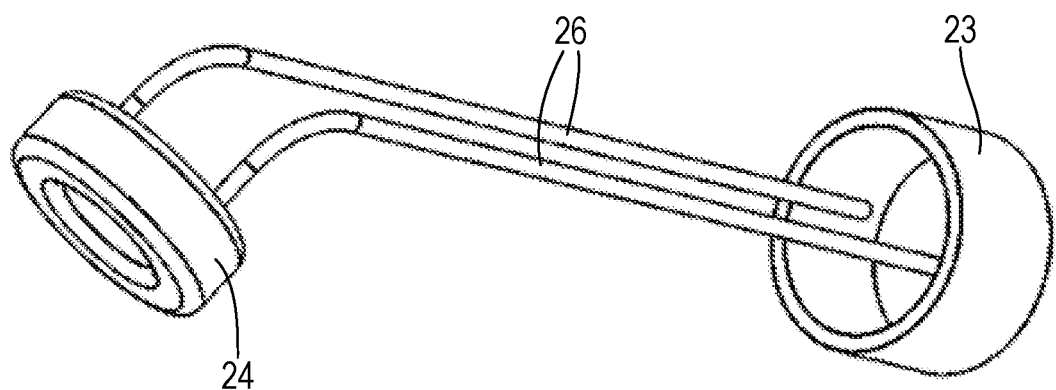
FIG. 12 is a perspective view of the closing ring, control ring, and push-pull cable which can be combined with the portion of the tool shown in FIG. 11.

In the illustrated embodiment, manually pulling on control ring 24 in the direction of ball 21 causes closing ring 23 to ride over arms 22, thereby forcing them closed. The closed position is shown in FIG. 11 with the rings and cables removed. Rings 23 and 24 and cables 26 may be formed as a separate assembly as shown in FIG. 12.

The various components of tool 15 may be comprised of injection molded parts using a biocompatible thermoplastic, metallic parts (e.g., stainless steel), or a combination of plastic and metallic parts.

What is claimed is:

1. A stabilization tool for suturing a vessel, comprising:
a central shaft having a mounting element at a first end;
a plurality of retractable arms having distal ends affixed to a second end of the central shaft, wherein the retractable arms are each comprised of a resilient beam having a natural curved shape corresponding to a maximum extended position, wherein the retractable arms are movable between a nested position flanking the central shaft and a range of extended positions wherein proximal ends of the retractable arms are spaced away from the central shaft, wherein the second end is configured to be inserted inside the vessel in the nested position, wherein the retractable arms are configured to support an inside diameter of the vessel when in the range of extended positions during suturing, and wherein the second end is configured to be removed from the vessel in the nested position after suturing;
a closing ring slidable over the retractable arms from a deployed position adjacent the second end of the central shaft to a retracted position spaced away from the second end;
a control ring mounted on the central shaft between the retractable arms and the first end adapted to slide along the central shaft under manual control; and
a push-pull cable connecting the control ring and the closing ring so that motion of the control ring is replicated by the closing ring to reconfigure the retractable arms between the nested position and an extended position within the range of extended positions.

2. The stabilization tool of claim 1 wherein the retractable arms are comprised of spring grade stainless steel.

3. The stabilization tool of claim 1 wherein the retractable arms are comprised of plastic.

4. A stabilization tool for suturing a vessel, comprising:
a central shaft having a mounting element at a first end;
a plurality of retractable arms having distal ends affixed to a second end of the central shaft, wherein the retractable arms are movable between a nested position flanking the central shaft and a range of extended positions wherein proximal ends of the retractable arms are spaced away from the central shaft;
a closing ring slidable over the retractable arms from a deployed position adjacent the second end of the central shaft to a retracted position spaced away from the second end;
a control ring mounted on the central shaft between the retractable arms and the first end adapted to slide along the central shaft under manual control; and
a push-pull cable connecting the control ring and the closing ring so that motion of the control ring is replicated by the closing ring to reconfigure the retractable arms between the nested position and an extended position within the range of extended positions.

5. The stabilization tool of claim 4 wherein the central shaft includes an intermediate bend between the retractable arms and the control ring.

6. The stabilization tool of claim 5 further comprising:
a cable guide projecting from the central shaft at the intermediate bend for slidably receiving the push-pull cable.

7. The stabilization tool of claim 4 further comprising:
a second push-pull cable connecting the control ring and the closing ring and placed symmetrically on an opposite side of the central shaft.

8. The stabilization tool of claim 4 wherein the push-pull cable is comprised of a metallic wire.

9. The stabilization tool of claim 8 wherein the metallic wire is comprised of stainless steel.

10. The stabilization tool of claim 4 adapted to expand a vascular graft having a predetermined inside diameter, and wherein the retractable arms are configured to provide a maximum extended position defining a perimeter at the proximal ends corresponding to the predetermined inside diameter.

11. The stabilization tool of claim 10 wherein the predetermined inside diameter is between about 25 mm and about 35 mm.

12. The stabilization tool of claim 10 wherein the predetermined inside diameter is about 30 mm.

* * * * *